(12) United States Patent
Schroeder (10) Patent No.: US 12,419,209 B2
(45) Date of Patent: Sep. 23, 2025

(54) SYSTEM AND METHOD FOR REDUCING SHANK WEAR ON AN AGRICULTURAL IMPLEMENT

(71) Applicant: CNH Industrial America LLC, New Holland, PA (US)

(72) Inventor: Brittany Schroeder, Bunker Hill, IN (US)

(73) Assignee: CNH Industrial America LLC, New Holland, PA (US)

( * ) Notice: Subject to any disclaimer, the term of this patent is extended or adjusted under 35 U.S.C. 154(b) by 126 days.

(21) Appl. No.: 18/221,648

(22) Filed: Jul. 13, 2023

(65) Prior Publication Data

US 2025/0017130 A1 Jan. 16, 2025

(51) Int. Cl.
| | | |
|---|---|---|
| A01B 79/02 | (2006.01) | |
| A01B 47/00 | (2006.01) | |
| A01B 79/00 | (2006.01) | |
| G01N 33/24 | (2006.01) | |

(52) U.S. Cl.
CPC ............ *A01B 79/02* (2013.01); *G01N 33/24* (2013.01); *G01N 33/245* (2024.05)

(58) Field of Classification Search
None
See application file for complete search history.

(56) References Cited

U.S. PATENT DOCUMENTS

| | | |
|---|---|---|
| 855,389 A | 5/1907 | Dawkins |
| 2,588,561 A | 3/1952 | Opp et al. |
| 9,405,039 B2 | 8/2016 | Anderson |
| 10,188,045 B1 * | 1/2019 | Flagler .................. A01M 3/025 |
| 10,729,052 B1 * | 8/2020 | Lund ...................... A01C 5/062 |
| 11,191,202 B2 | 12/2021 | Henry |
| 11,284,612 B2 | 3/2022 | Fox et al. |
| 11,369,052 B2 | 6/2022 | Cozza et al. |
| 11,497,154 B1 | 11/2022 | Lund et al. |

(Continued)

FOREIGN PATENT DOCUMENTS

| | | |
|---|---|---|
| CN | 107466574 A | 12/2017 |
| DE | 758514 C | 11/1953 |

(Continued)

OTHER PUBLICATIONS

Co-Pending U.S. Appl. No. 18/221,657, filed Jul. 13, 2023.

*Primary Examiner* — Jared Fureman
*Assistant Examiner* — Aqeel H Bukhari
(74) *Attorney, Agent, or Firm* — Dority & Manning, P.A.

(57) ABSTRACT

A system for reducing shank wear on an agricultural implement includes a shank configured to be moved through soil within a field as the agricultural implement travels across the field. Furthermore, the system includes an electrode embedded within the shank. Additionally, the system includes a sensor configured to generate data indicative of a soil moisture content of a portion of the field and a computing system communicatively coupled to the sensor. As such, the computing system is configured to determine the soil moisture content of the field based on the data generated by the sensor. Moreover, the computing system is configured to control a flow of electricity at least one of to or from the electrode based on the determined soil moisture content such that an electric field is induced on at least a portion of a forward outer surface of the shank.

17 Claims, 7 Drawing Sheets

(56) References Cited

U.S. PATENT DOCUMENTS

2020/0084953 A1* 3/2020 Stanhope ............... A01B 63/32
2021/0045281 A1   2/2021 Glovier
2021/0169064 A1* 6/2021 Fox ....................... A01B 47/00

FOREIGN PATENT DOCUMENTS

DE   102008026159 A1   12/2009
RU        2421955 C1    6/2011
SU        1250177 A1    8/1986

* cited by examiner

SYSTEM AND METHOD FOR REDUCING SHANK WEAR ON AN AGRICULTURAL IMPLEMENT

FIELD OF THE INVENTION

The present disclosure generally relates to agricultural implements and, more particularly, to systems and methods for reducing shank wear on an agricultural implement.

BACKGROUND OF THE INVENTION

It is well known that, to attain the best agricultural performance from a field, a farmer must cultivate the soil, typically through a tillage operation. Modern farmers perform tillage operations by pulling an agricultural implement behind an agricultural work vehicle, such as a tractor. Agricultural implements typically include one or more ground-engaging tools, such as shanks, harrow disk blades, leveling blades, and/or the like, that are configured to loosen and/or otherwise agitate the soil to prepare the field for subsequent planting operations.

During tillage operations, as the agricultural implement is towed across the field, the soil slides over the forward outer surfaces of the shanks of the implement. The adhesional forces between the soil and the shanks can create significant friction between the soil and the shanks. This friction, in turn, causes the shanks to incur wear. Replacing worn shanks (or components thereof) is costly and time-consuming process.

Accordingly, a system and method for reducing shank wear on an agricultural implement would be welcomed in the technology.

SUMMARY OF THE INVENTION

Aspects and advantages of the technology will be set forth in part in the following description, or may be obvious from the description, or may be learned through practice of the technology.

In one aspect, the present subject matter is directed to an agricultural implement. The agricultural implement, in turn, includes a frame and a shank supported on the frame, with the shank configured to be moved through soil within a field as the agricultural implement travels across the field. Furthermore, the agricultural implement includes an electrode embedded within the shank. Additionally, the agricultural implement includes a sensor configured to generate data indicative of a soil moisture content of a portion of the field and a computing system communicatively coupled to the sensor. In this respect, the computing system is configured to determine the soil moisture content of the field based on the data generated by the sensor. Moreover, the computing system is configured to control a flow of electricity at least one of to or from the electrode based on the determined soil moisture content such that an electric field is induced on at least a portion of a forward outer surface of the shank.

In another aspect, the present subject matter is directed to a system for reducing shank wear on an agricultural implement. The system includes a shank configured to be moved through soil within a field as the agricultural implement travels across the field. In addition, the system includes an electrode embedded within the shank. Furthermore, the system includes a sensor configured to generate data indicative of a soil moisture content of a portion of the field and a computing system communicatively coupled to the sensor. As such, the computing system is configured to determine the soil moisture content of the field based on the data generated by the sensor. Additionally, the computing system is configured to control a flow of electricity at least one of to or from the electrode based on the determined soil moisture content such that an electric field is induced on at least a portion of a forward outer surface of the shank.

In a further aspect, the present subject matter is directed to a method for reducing shank wear on an agricultural implement. The agricultural implement, in turn, includes a shank configured to be moved through soil within a field as the agricultural implement travels across the field. Moreover, the agricultural implement further includes an electrode embedded within the shank. The method includes receiving, with a computing system, sensor data indicative of a soil moisture content of a portion of the field. In addition, the method includes determining, with the computing system, the soil moisture content of the field based on the received sensor data. Furthermore, the method includes controlling, with the computing system, a flow of electricity at least one of to or from the electrode based on the determined soil moisture content such that an electric field is induced on at least a portion of a forward outer surface of the shank.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which.

Repeat use of reference characters in the present specification and drawings is intended to represent the same or analogous features or elements of the present technology.

DETAILED DESCRIPTION OF THE DRAWINGS

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield still a further embodiment. Thus, it is intended that the present invention covers such modifications and variations as come within the scope of the appended claims and their equivalents.

In general, the present subject matter is directed to a system and a method for reducing or preventing soil adhesion on an agricultural implement. As will be described below, the agricultural implement includes one or more shanks configured to be moved through the soil within a field as the agricultural implement travels across the field (e.g., to perform an agricultural operation thereon). Furthermore, the agricultural implement includes one or more electrodes embedded within the shank(s).

Additionally, a computing system of the disclosed system is configured to control the flow of electricity to and/or from the electrode(s) such that an electric field(s) is induced on the forward outer surface(s) of the shanks(s). Specifically, in several embodiments, the computing system is configured to receive sensor data indicative of a soil moisture content of a portion(s) of the field (e.g., that is forward of the shank(s)). Moreover, the computing system is configured to determine the soil moisture content of the field based on the received sensor data. Thereafter, the computing system is configured to control one or more flow control devices (e.g., one or more transistors, relays, switches, rheostats, power converters, etc.) to control the flow of electricity to and/or from the electrode(s) based on the determined soil moisture content. This, in turn, induces an electric field(s) on at least a portion(s) of the forward outer surface(s) of the shank(s). For example, in some embodiments, the computing system may determine the strength of the electric field(s) to be induced based on the soil moisture content. Thereafter, the computing system may control the flow of electricity such that the electric field(s) induced on the shank(s) has the determined strength.

The disclosed system and method improve the operation of the agricultural implement. More specifically, water present within the soil creates adhesional forces between the soil and the shank(s) of the agricultural implement. This, in turn, creates friction between the shank(s) and the soil as the soil slides over the forward outer surface(s) of the shank(s). Such friction causes the shank(s) to wear. Moreover, as the moisture content of the soil increases, the adhesional forces between the soil and the shank(s) (and, thus, the associated friction and wear) similarly increase. As described above, the disclosed system and method induce an electric field(s) on the forward outer surface(s) of the shank(s). Moreover, by using the soil moisture content, the strength of the electric field(s) induced on the shank(s) can be adjusted to ensure that electroosmosis is occurring on the shank(s). Electroosmosis, in turn, reduces the adhesional forces between the soil and the shank(s) and, thus, the friction between the shank(s), thereby reducing the wear incurred by the shank(s) and increasing the service life of the shank(s).

Figure 1:
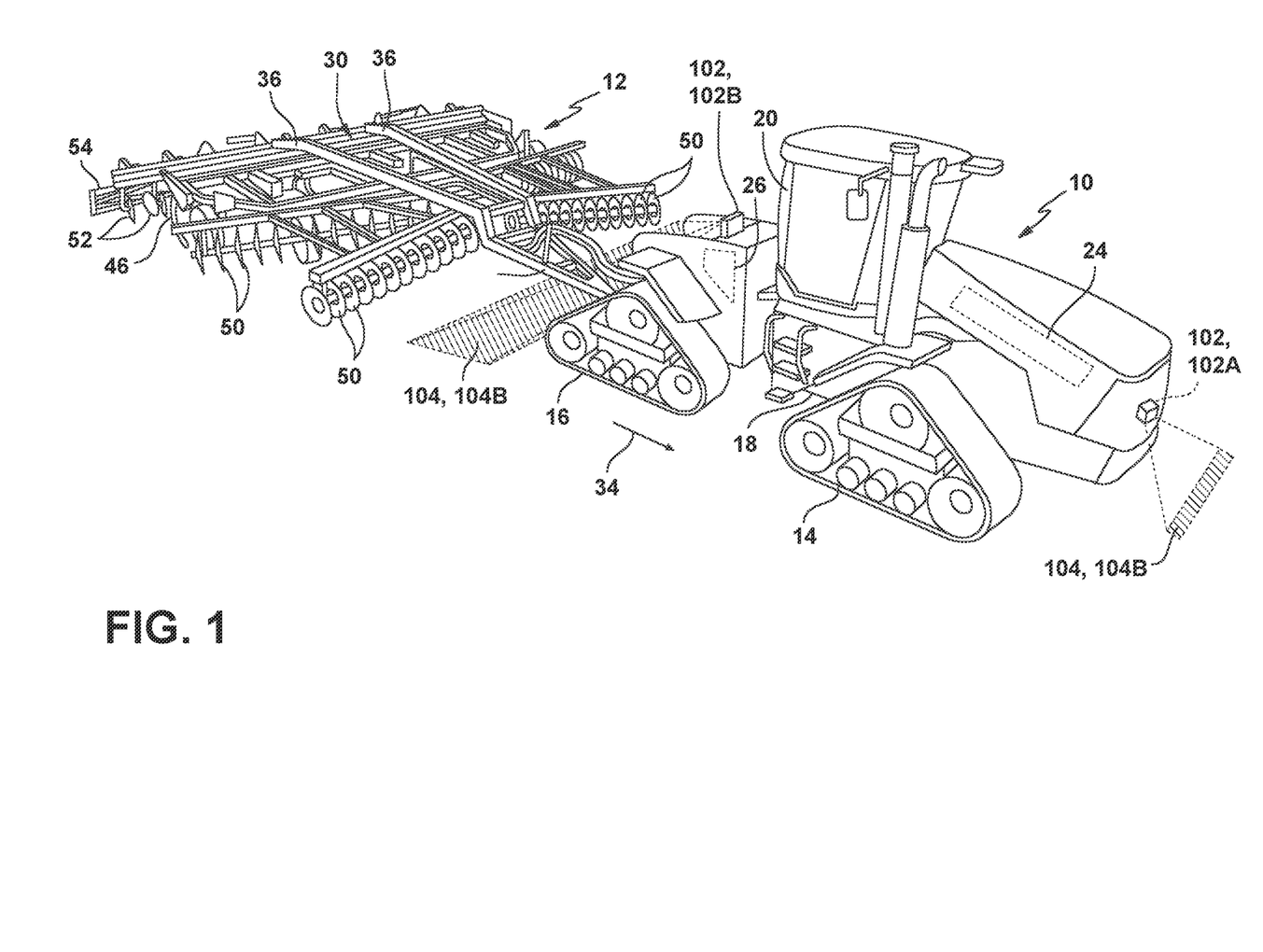
FIG. 1 illustrates a perspective view of one embodiment of an agricultural implement coupled to a work vehicle in accordance with aspects of the present subject matter.
Figure 2:
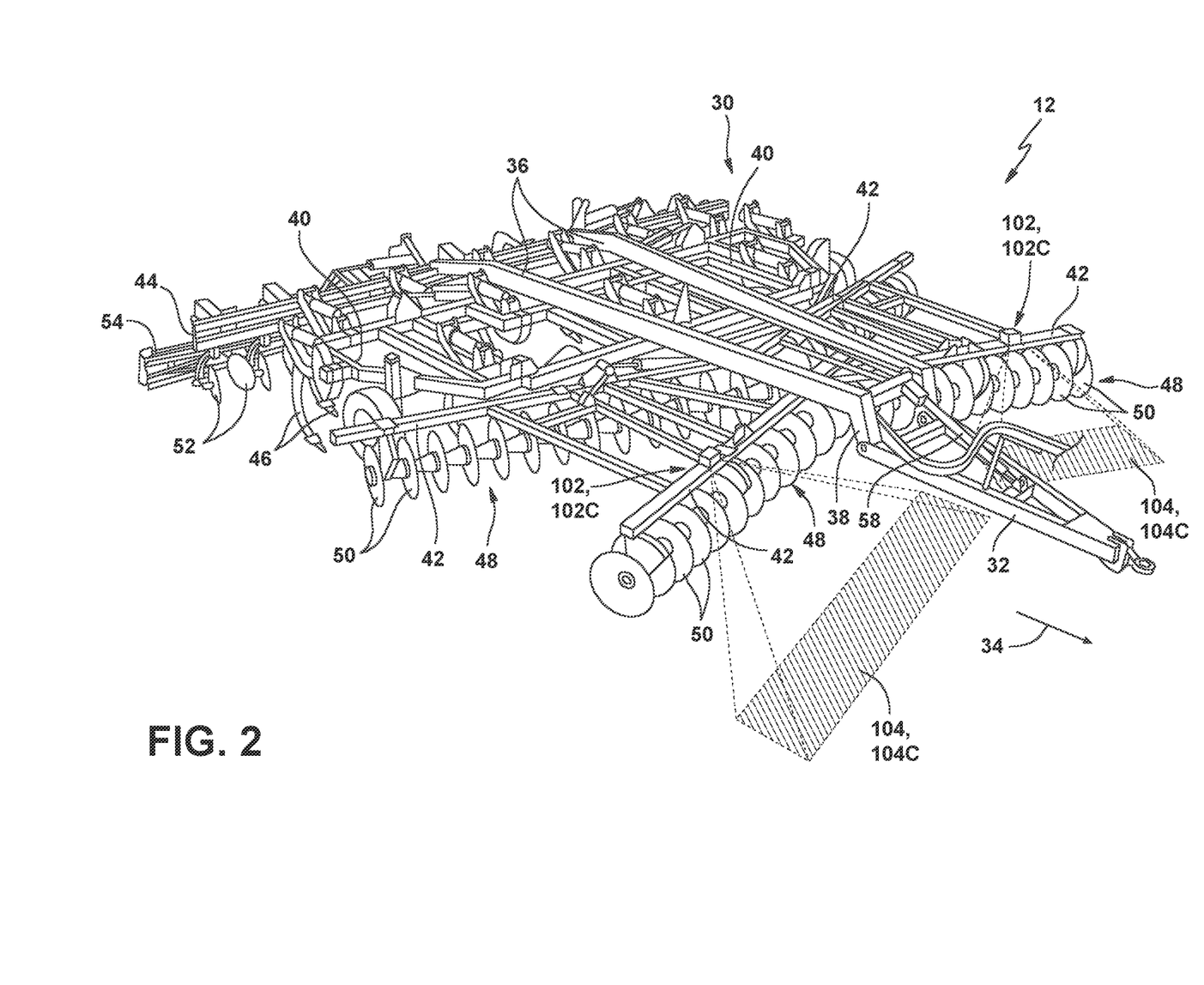
FIG. 2 illustrates another perspective view of the agricultural implement shown in FIG. 1, particularly illustrating various ground-engaging tools of the implement.

Referring now to drawings, FIGS. 1 and 2 illustrate perspective views of one embodiment of a work vehicle 10 and an associated agricultural implement 12. Specifically, FIG. 1 illustrates a perspective view of the work vehicle 10 towing the agricultural implement 12 (e.g., across a field). Additionally, FIG. 2 illustrates a perspective view of the agricultural implement 12 shown in FIG. 1.

As shown, in the illustrated embodiment, the work vehicle 10 is configured as an agricultural tractor and the agricultural implement 12 is configured as a tillage implement (e.g., a disk ripper). However, in other embodiments, the work vehicle 10 may be configured as any other suitable vehicle configured to tow an agricultural implement. Similarly, the agricultural implement 12 may be configured as any other suitable type of implement, such as another type of tillage implement, a seed-planting implement, a fertilizing implement, or the like.

As particularly shown in FIG. 1, the work vehicle 10 includes a pair of front track assemblies 14, a pair or rear track assemblies 16, and a frame or chassis 18 coupled to and supported by the track assemblies 14, 16. An operator's cab 20 may be supported by a portion of the chassis 18 and may house various input devices for permitting an operator to control the operation of one or more components of the work vehicle 10 and/or one or more components of the agricultural implement 12. Additionally, the work vehicle 10 may include an engine 24 and a transmission 26 mounted on the chassis 18. The transmission 26 may be operably coupled to the engine 24 and may provide variably adjusted gear ratios for transferring engine power to the track assemblies 14, 16 via a drive axle assembly (not shown) (or via axles if multiple drive axles are employed).

Moreover, as shown in FIGS. 1 and 2, the agricultural implement 12 includes a carriage frame assembly 30 configured to be towed by the work vehicle 10 via a pull hitch or tow bar 32 in a direction of travel of the vehicle (e.g., as indicated by arrow 34). In this respect, the carriage frame assembly 30 may be configured to support a plurality of ground-engaging tools, such as a plurality of shanks, disk blades, leveling blades, basket assemblies, and/or the like. As such, the various ground-engaging tools may be configured to perform an agricultural operation (e.g., a tillage operation) on the field across which the agricultural implement 12 is being towed.

As particularly shown in FIG. 2, the carriage frame assembly 30 may include aft extending carrier frame members 36 coupled to the tow bar 32. In addition, reinforcing gusset plates 38 may be used to strengthen the connection between the tow bar 32 and the carrier frame members 36. In several embodiments, the carriage frame assembly 30 may support a central frame 40, a forward frame 42 positioned forward of the central frame 40 relative to the direction of travel 34 of the work vehicle 10, and an aft frame 44 positioned aft of the central frame 40 relative to the direction of travel 34 of the work vehicle 10. As shown in FIG. 2, in one embodiment, the central frame 40 may correspond to a shank frame configured to support a plurality of ground-engaging shanks 46. In such an embodiment, the shanks 46 may be configured to be moved through the soil in the field as the agricultural implement 12 is towed across the field, thereby tilling the soil. However, in other embodiments, the central frame 40 may be configured to support any other suitable ground-engaging tools.

Additionally, as shown in FIG. 2, in one embodiment, the forward frame 42 may correspond to a disk frame configured to support various gangs or sets 48 of disk blades 50. In such an embodiment, each disk blade 50 may, for example, include both a concave side (not shown) and a convex side (not shown). In addition, the various gangs 48 of disk blades 50 may be oriented at an angle relative to the travel direction 34 of the work vehicle 10 to promote more effective tilling of the soil. However, in other embodiments, the forward frame 42 may be configured to support any other suitable ground-engaging tools.

Moreover, like the central and forward frames 40, 42, the aft frame 44 may also be configured to support a plurality of ground-engaging tools. For instance, in the illustrated embodiment, the aft frame is configured to support a plurality of leveling blades 52 and rolling (or crumbler) basket assemblies 54. However, in other embodiments, any other suitable ground-engaging tools may be coupled to and supported by the aft frame 44, such as a plurality closing disks.

Additionally, as shown in FIGS. 1 and 2, the work vehicle 10 and/or the agricultural implement 12 may include one or more sensors 102 coupled thereto and/or supported thereon. In general, the sensor(s) 102 is configured to generate data indicative of the soil moisture content of the field across which the vehicle/implement 10/12 are traveling. Specifically, in several embodiments, the sensor(s) 102 may be provided in operative association with the work vehicle 10 such that the sensor(s) 102 has a field(s) of view 104 directed towards a portion(s) of the field disposed in front of, behind, and/or along one or both of the sides of the work vehicle 10. Additionally, or alternatively, the sensor(s) 102 may be provided in operative association with the agricultural implement 12 such that the sensor(s) has a field(s) of view 104 directed towards a portion(s) of the field disposed in front of the agricultural implement 12 as the agricultural implement 12 is being towed across the field. As such, the sensor(s) 102 may generate soil moisture data associated with one or more portion(s) of the field in front of the agricultural implement 12 (and, more specifically, the shanks 46 of the agricultural implement 12) as the vehicle/implement 10/12 travels across the field.

In general, the sensor(s) 102 may correspond to any suitable device(s) configured to generate data indicative of the soil moisture content of the field. For example, in several embodiments, the sensor(s) 102 may be configured as an optical sensor(s) configured to detect one or more characteristics of the light reflected by the soil, with such characteristics generally being indicative of the soil moisture content. However, in alternative embodiments, the sensor(s) 102 may be configured as any other suitable device(s) for sensing or detecting the soil moisture content of the field.

The work vehicle 10 and/or the agricultural implement 12 may include any number of sensors 102 provided at any suitable location(s) that allows soil moisture data to be generated as the work vehicle 10 and the agricultural implement 12 traverse the field. In this respect, FIGS. 1 and 2 illustrate example locations for mounting the sensor(s) 102 for generating soil moisture data for the portion of the field forward of the agricultural implement 12 relative to the direction of travel 34.

For example, as shown in FIG. 1, in one embodiment, one or more sensors 102A may be coupled to the front of the work vehicle 10 such that the sensor(s) 102A has a field(s) of view 104A that allows for the generation of data indicative of the soil moisture content of an adjacent area or portion of the field disposed in front of the work vehicle 10 and, thus, in front of the agricultural implement 12. For instance, the field(s) of view 104A of the sensor(s) 102A may be directed outwardly from the front of the work vehicle 10 along a plane or reference line that extends generally parallel to the travel direction 34 of the work vehicle 10. In addition to the sensor(s) 102A (or as an alternative thereto), one or more sensors 102B may be coupled to the rear of the work vehicle 10 such that the sensor(s) 102B has a field(s) of view 104B that allows for the generation of data indicative of the soil moisture content of an adjacent area or portion of the field disposed aft of the work vehicle 10 and forward of the agricultural implement 12. For instance, the field(s) of view 104B of the sensor(s) 102B may be directed outwardly from the rear of the work vehicle 10 along a plane or reference line that extends generally parallel to the travel direction 34 of the work vehicle 10.

In addition to the sensor(s) 102A, 102B (or as an alternative thereto), one or more sensors 102C may also be coupled to the front of the agricultural implement 12 such that the sensor(s) 102C has a field(s) of view 104C that allows for the generation of data indicative of the soil moisture content of an adjacent area or portion of the field disposed in front of the agricultural implement 12. For instance, the field(s) of view 104C of the sensor(s) 102C may be directed outwardly from the front of the agricultural implement 12 along a plane or reference line that extends generally perpendicular to the travel direction 34 of the work vehicle 10.

However, in alternative embodiments, the sensor(s) 102 may be installed at any other suitable location(s) that allows the device(s) to generate data indicative of the soil moisture content of a portion(s) of the field forward of the agricultural implement 12 (e.g., forward of the shanks 46 of the agricultural implement 12).

Figure 3:
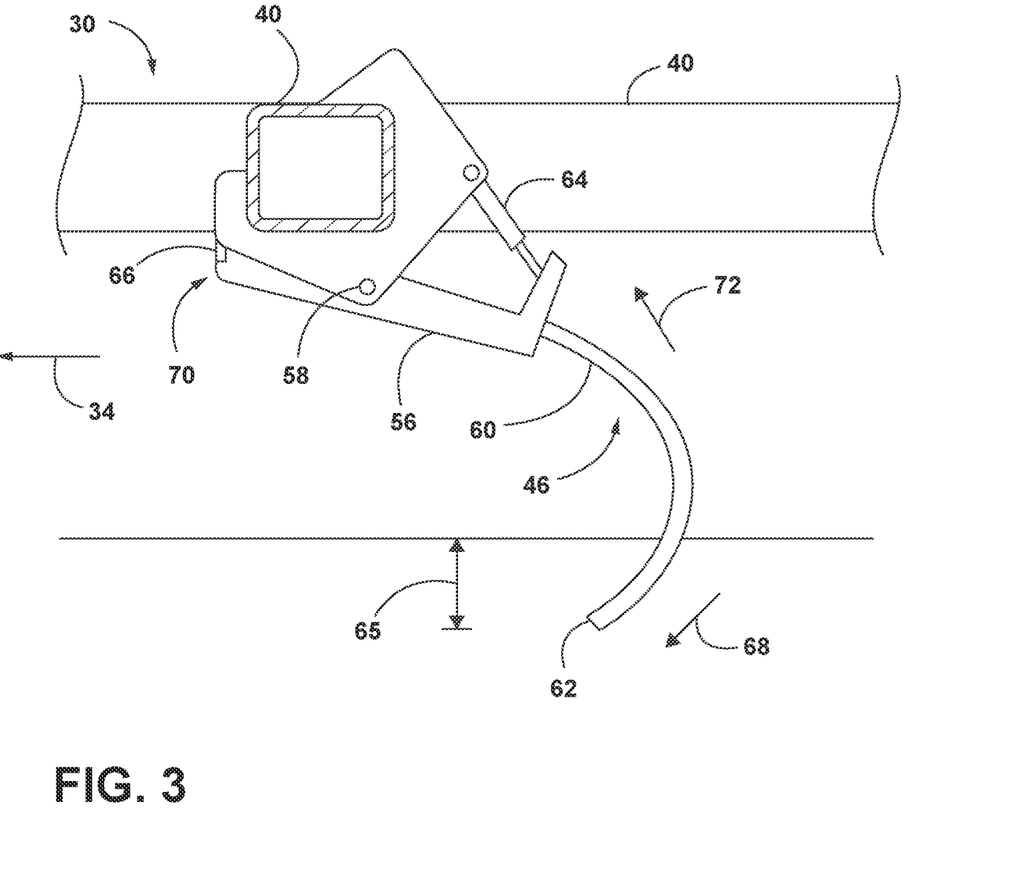
FIG. 3 illustrates a front view of one embodiment of a shank of an agricultural implement in accordance with aspects of the present subject matter.

Referring now to FIG. 3, a side view of one embodiment of one of the shanks 46 is illustrated in accordance with aspects of the present subject matter. As shown, the shank 46 includes a base portion 56 pivotably coupled to the central frame 40 of the carriage frame assembly 30 (e.g., at a pivot joint 58). Furthermore, the shank 46 may include a ground-engaging portion 60 extending from the base portion 56 along a curved or arcuate profile. The ground-engaging portion 60 may include a tip 62 that is configured to penetrate into or otherwise engage the soil as the implement 10 travels across the field. In this respect, the soil within the field may slide over the outer surfaces of and flow around the shank 46 as the shank 46 is pulled through the soil. However, in alternative embodiments, the shank 46 may be configured in any other suitable manner.

In several embodiments, an actuator 64 may be coupled between the central frame 40 and the shank 46. As such, the actuator 64 may be configured to bias the shank 46 to a predetermined tool position (e.g., a home or base position) relative to the central frame 40. In general, the predetermined tool position may correspond to a tool position in which the shank 46 penetrates the soil or ground to a selected or desired depth (indicated by arrow 65). In several embodiments, the predetermined ground-engaging tool position may be set by a mechanical stop 66. In operation, the actuator 64 may permit relative movement between the shank 46 and the central frame 40. For example, the actuator 64 may be configured to bias the shank 46 to pivot relative to the central frame 40 in a first pivot direction (indicated by arrow 68) until an end 70 of the base portion 56 of the shank 46 contacts the stop 66. The actuator 64 may also allow the shank 46 to pivot away from the predetermined tool position (e.g., to a shallower depth of penetration), such as in a second pivot direction (indicated by arrow 72) opposite the first pivot direction 68, when encountering rocks or other impediments in the field.

The actuator 64 may be configured as any suitable type of actuator configured to bias the shank 46 relative to the central frame 40 or otherwise apply a force to the shank 46. For example, in several embodiments, the actuator 64 may be configured as a suitable fluid-driven actuator, such as a suitable hydraulic or pneumatic cylinder. However, in alternative embodiments, the actuator 64 may be configured as any other suitable type of actuator, such as an electric linear actuator. Additionally, in a further embodiment, a spring (not shown) may be configured to bias the shank 46 relative to the central frame 40 in lieu of the actuator 64.

The configuration of the work vehicle 10 and the agricultural implement 12 described above and shown in FIGS. 1-3 is provided only to place the present subject matter in an exemplary field of use. Thus, the present subject matter may be readily adaptable to any manner of vehicle and/or implement configuration.

Figure 4:
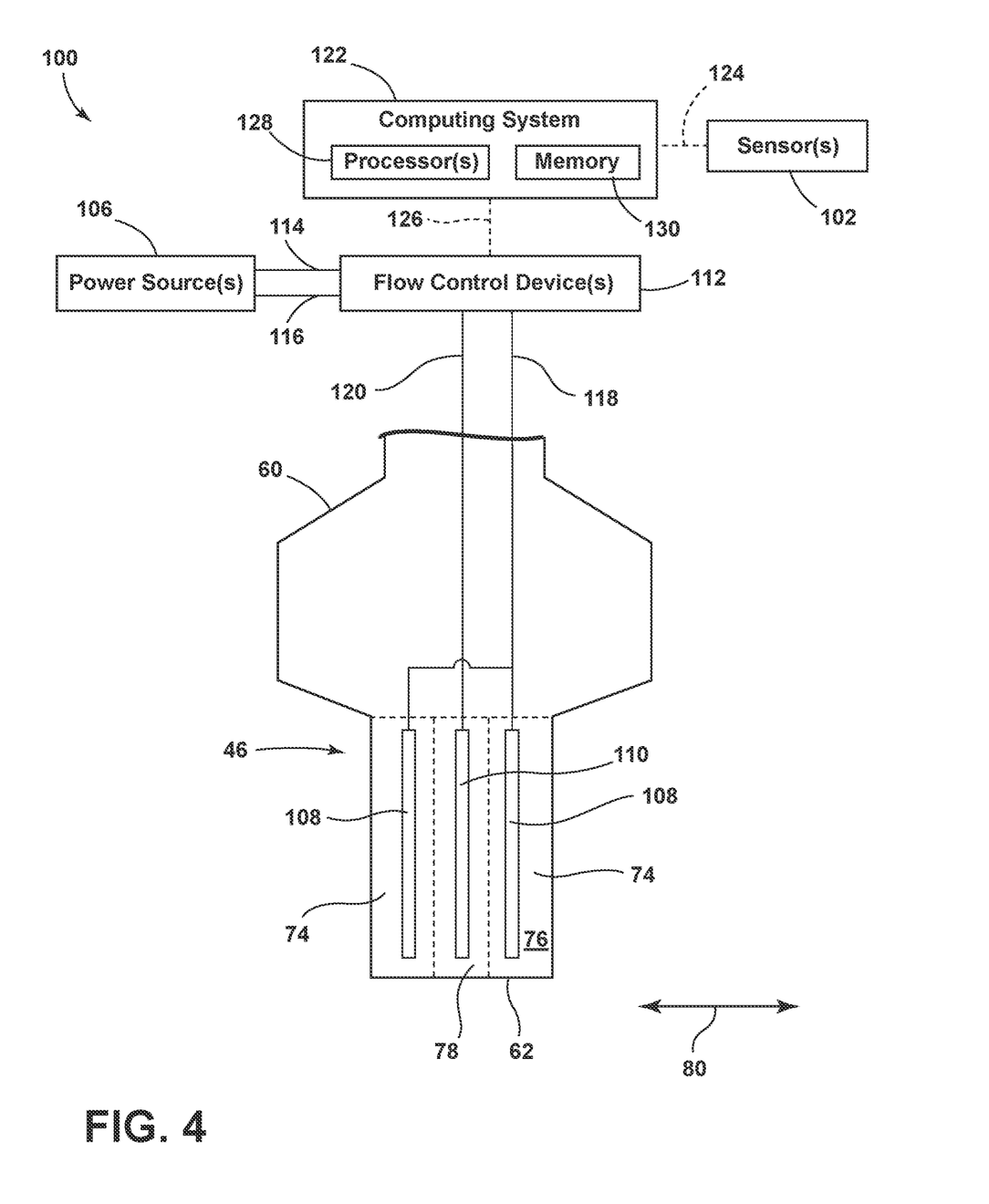
FIG. 4 illustrates a schematic view of one embodiment of a system for reducing shank wear on an agricultural implement in accordance with aspects of the present subject matter.

Referring now to FIG. 4, a schematic view of one embodiment of a system 100 for reducing shank wear on an agricultural implement is illustrated in accordance with aspects of the present subject matter. In general, the system 100 will be described herein with reference to the work vehicle 10 and the agricultural implement 12 described above with reference to FIGS. 1-3. However, it should be appreciated by those of ordinary skill in the art that the disclosed system 100 may generally be utilized with work vehicles having any other suitable vehicle configuration and/or with agricultural implements having any other suitable implement configuration.

As shown in FIG. 4, the system 100 includes one or more power sources 106. In general, the power source(s) 106 is configured to generate electric current, which is, in turn, used to induce an electric field(s) on a portion(s) of one or more of the shanks 46 of the agricultural implement 12. As such, the power source(s) 106 may correspond to one or more batteries, alternators, generators, and/or the like.

Furthermore, in several embodiments, the system 100 includes one or more first electrodes 108 and one or more second electrodes 110 embedded within the shank(s) 46. In general, each first electrode 108 is configured to operate as one of an anode or a cathode, while each second electrode 110 is configured to operate as the other of the anode or cathode. In this respect, one of a positive or negative electric field is induced on a portion(s) 74 of a forward outer surface(s) 76 of the shank(s) 46 adjacent to the first electrode(s) 108. Conversely, the other of the positive or negative electric field is induced on a portion(s) 78 of the forward outer surface(s) 76 of the shank(s) 46 adjacent to the second electrode(s) 110. As will be described below, in several embodiments, the polarities of the electric fields being induced on the outer surface(s) 78 of the shank(s) 46 is alternated. For example, during a given period of time, the first electrode(s) 108 operates as an anode(s) such that a positive electric field(s) is induced on the portion(s) 74 of the forward outer surface(s) 76 of the shank(s) 46 adjacent thereto. Simultaneously, during the given period of time, the second electrode(s) 110 operates as a cathode(s) such that a negative electric field(s) is induced on the portion(s) 78 of the forward outer surface(s) 76 of the shank(s) 46 adjacent thereto. Thereafter, during a subsequent period of time, the first electrode(s) 108 operates as a cathode(s) such that a negative electric field(s) is induced on the portion(s) 74 of the forward outer surface(s) 76 of the shank(s) 46 adjacent thereto. Simultaneously, during the subsequent period of time, the second electrode(s) 110 operates as an anode(s) such that a positive electric field(s) is induced on the portion(s) 78 of the forward outer surface(s) 76 of the shank(s) 46 adjacent thereto. This alternating pattern is repeated as the shank(s) 46 is moved though the soil within the field. Such alternating electric fields, in turn, cause electroosmosis to occur on the forward outer surface(s) 76 of the shank(s) 46, which reduces the adhesional forces between the soil and the shank(s) 46 and, thus, the friction between the shank(s) 46 and the soil.

Each shank 46 may include any suitable number of first electrodes 108 and/or any suitable number of second electrodes 110. For example, as shown in FIG. 4, the illustrated shank 46 includes two first electrodes 108 spaced apart from each other along a lateral direction (e.g., as indicated by arrow 80) of the shank 46, with the lateral direction 80 generally being perpendicular to the direction of travel 34 of the vehicle/implement 10/12. Additionally, as shown in FIG. 4, the illustrated shank 46 includes one second electrodes 110. Moreover, the first and second electrodes 108, 110 are interdigitated in the lateral direction 80 such that the second electrode 110 is positioned between the first electrodes 108. However, in alternative embodiments, the shank(s) 46 may include more or less first electrodes 108 and/or more or less second electrodes 110. Additionally, the first and/or second electrodes 108, 110 may be arranged in any other suitable manner.

Moreover, the first and second electrodes 108, 110 may have any suitable construction and/or be embedded in the shank(s) 46 in any suitable manner. For example, as shown in FIG. 4, the first and second electrodes 108, 110 are configured as slender, rod-like metallic components that extend the forward outer surface 76 of the illustrated shank 46. Furthermore, in the illustrated embodiment, the first and second electrodes 108, 110 are of similar construction. However, in alternative embodiments, the first and second electrodes 108, 110 may be of any other suitable construction and/or be embedded in the shank(s) 46 in any other suitable manner.

In addition, the system 100 includes one or more flow control devices 112. In general, the flow control device(s) 112 is configured to control the flow of electric current between the power source(s) 106 and the first and second electrodes 108, 110. In this respect, the flow control device(s) 112 may be configured as any suitable device(s) configured to control the flow of electric current, such as one or more switches, one or more relays, one or more transistors, one or more power converters, one or more rheostats, and/or the like. As will be described below, by controlling the operation of the flow control device(s) 112, the flow of electricity to the shank(s) 46 can be adjusted, thereby allowing the magnitudes of the electric fields induced on the shank(s) 46 to be controlled.

Furthermore, the system 100 may include one or more electric wires or cables to facilitate the flow of electric current between the power source(s) 106 and the first and second electrodes 108, 110. For example, in the illustrated embodiment, electric wires 114, 116 may electrically couple the power source(s) 106 and the flow control device(s) 112. Additionally, an electric wire(s) 118 may electrically couple the flow control device(s) 112 to the first electrode(s) 108. Similarly, an electric wire(s) 120 may electrically couple the flow control device(s) 112 to the second electrode(s) 110. In one embodiment, the electric wires 118, 120 may be routed along the central frame 40 and/or through shank(s) 46 (e.g., through the base portion(s) 56 of the shank(s) 46).

In operation, alternating positive and negative electric fields may be induced on the forward outer surface(s) 76 of the shank(s) 46. More specifically, as the agricultural implement 12 travels across the field, the shank(s) 46 is moved through the soil such that the soil slides over the forward outer surface(s) 76 of the shank(s) 46. During a given period of time, the flow control device(s) 112 is actuated or otherwise adjusted such that the first electrode(s) 108 acts as an anode(s) and the second electrode(s) 110 acts as a cathode(s). In such instances, the power source(s) 106 may cause electric current to flow from first electrode(s) 108 to the second electrode(s) 110, thereby inducing a positive electric field in the portion(s) 74 of the forward outer surface(s) 76 of the shank(s) 46 adjacent to the first electrode(s) 108 and a negative electric field in the portion(s) 78 of the forward outer surface(s) 76 of the shank(s) 46 adjacent to the second electrode(s) 110. During a subsequent period of time, the flow control device(s) 112 is again actuated or otherwise adjusted such that the first electrode(s) 108 acts as a cathode(s) and the second electrode(s) 110 acts as an anode(s). In such instances, the power source(s) 106 may cause electric current to flow from second electrode(s) 110 to the first electrode(s) 108, thereby inducing a positive electric field in the portion(s) 78 of the forward outer surface(s) 76 of the shank(s) 46 adjacent to the second electrode(s) 110 and a negative electric field in the portion(s) 74 of the outer surface(s) 76 of the shank(s) 46 adjacent to the first electrode(s) 108. During another subsequent period of time, the flow control device(s) 112 is further actuated or otherwise adjusted such that the first electrode(s) 108 acts as an anode(s) and the second electrode(s) 110 acts as a cathode(s) again and so on.

As mentioned above, the alternating positive and negative electric fields induced on the forward outer surface(s) 76 of the shank(s) 46 reduce the wear incurred by the shank(s) 46 during an agricultural operation. More specifically, water generally adheres to the portion(s) of the forward outer surface(s) 76 of the shank(s) 46 that are negatively charged and slides off of portion(s) of the forward outer surface(s) 76 of the shank(s) 46 that are positively charged. Such alternating adherence and a shedding of water on each portion 74, 78 of the forward outer surface(s) 76 of the shank(s) 46 results in electroosmosis, which reduces the adhesional forces between the shank(s) 46 and the soil. This, in turn, reduces the friction between the shank(s) 46 and the soil and, thus, the wear incurred by the shank(s) 46 during an agricultural operation. Reduced wear of the shank(s) 46 increases the service life of the shank(s) 46 and reduces the downtime of the implement 12.

Moreover, the system 100 includes a computing system 122 communicatively coupled to one or more components of the work vehicle 10, the agricultural implement 12, and/or the system 100 to allow the operation of such components to be electronically or automatically controlled by the computing system 122. For instance, the computing system 122 may be communicatively coupled to the sensor(s) 102 via a communicative link 124. As such, the computing system 122 may be configured to receive data from the sensor(s) 102 that is indicative of the soil moisture content of a portion(s) of the field positioned forward of the agricultural implement 12 (and, more specifically, the shank(s) 46 of the agricultural implement 12). Furthermore, the computing system 122 may be communicatively coupled to the flow control device(s) 112 via a communicative link 126. In this respect, the computing system 122 may be configured to control the operation of the flow control device(s) 112 to adjust the magnitude(s) of the electric field(s) being induced on the forward outer surface(s) 76 of the shank(s) 46. In addition, the computing system 122 may be communicatively coupled to any other suitable components of the work vehicle 10, the agricultural implement 12, and/or the system 100.

In general, the computing system 122 may comprise one or more processor-based devices, such as a given controller or computing device or any suitable combination of controllers or computing devices. Thus, in several embodiments, the computing system 122 may include one or more processor(s) 128 and associated memory device(s) 130 configured to perform a variety of computer-implemented functions. As used herein, the term "processor" refers not only to integrated circuits referred to in the art as being included in a computer, but also refers to a controller, a microcontroller, a microcomputer, a programmable logic circuit (PLC), an application specific integrated circuit, and other programmable circuits. Additionally, the memory device(s) 130 of the computing system 122 may generally comprise memory element(s) including, but not limited to, a computer readable medium (e.g., random access memory RAM)), a computer readable non-volatile medium (e.g., a flash memory), a floppy disk, a compact disk-read only memory (CD-ROM), a magneto-optical disk (MOD), a digital versatile disk (DVD) and/or other suitable memory elements. Such memory device(s) 130 may generally be configured to store suitable computer-readable instructions that, when implemented by the processor(s) 128, configure the computing system 122 to perform various computer-implemented functions, such as one or more aspects of the methods and algorithms that will be described herein. In addition, the computing system 122 may also include various other suitable components, such as a communications circuit or module, one or more input/output channels, a data/control bus and/or the like.

The various functions of the computing system 122 may be performed by a single processor-based device or may be distributed across any number of processor-based devices, in which instance such devices may be considered to form part of the computing system 122. For instance, the functions of the computing system 122 may be distributed across multiple application-specific controllers or computing devices, such as a navigation controller, an engine controller, a transmission controller, an implement controller, and/or the like.

Figure 5:
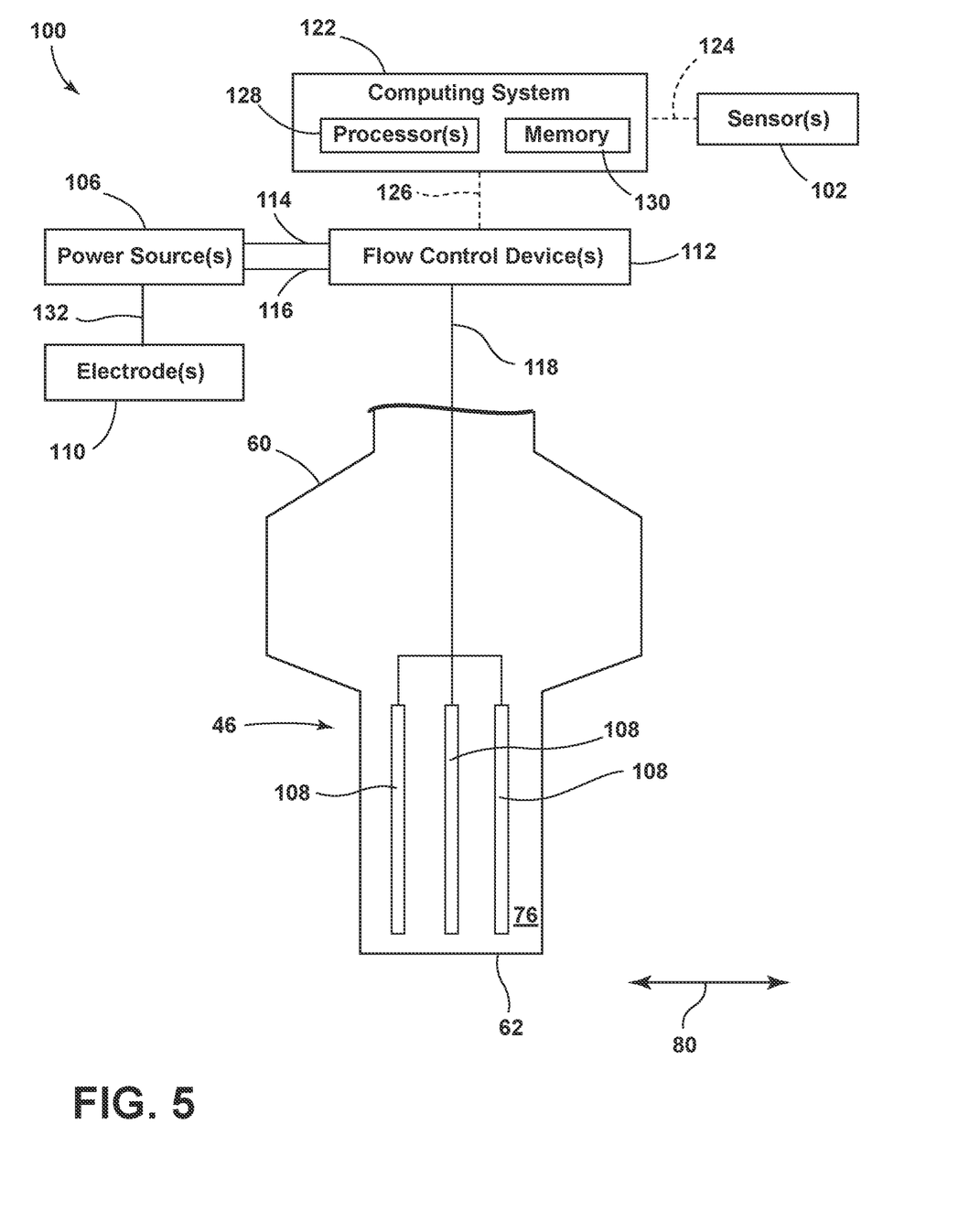
FIG. 5 illustrates a schematic view of another embodiment of a system for reducing shank wear on an agricultural implement in accordance with aspects of the present subject matter.

Referring now to FIG. 5, a schematic view of another embodiment of a system 100 for reducing shank wear on an agricultural implement is illustrated in accordance with aspects of the present subject matter. In general, the system 100 will be described herein with reference to the work vehicle 10 and the agricultural implement 12 described above with reference to FIGS. 1-3. However, it should be appreciated by those of ordinary skill in the art that the disclosed system 100 may generally be utilized with work vehicles having any other suitable vehicle configuration and/or with agricultural implements having any other suitable implement configuration.

In general, the embodiment of the system 100 shown in FIG. 5 is similar to the embodiment of the system 100 shown in FIG. 4. For example, like the system 100 shown in FIG. 5, the system 100 shown in FIG. 5 includes the power source(s) 106, the first electrode(s) 108, the second electrode(s) 110, the flow control device(s) 112, the electric wire(s) 114, the electric wire(s) 118, and the computing system 122.

However, unlike the system 100 of FIG. 4, in the system 100 shown in FIG. 5, the second electrode(s) 110 is positioned remote from the shank(s) 46 (e.g., not embedded in the shank(s) 46). Moreover, the second electrode(s) 110 are electrically coupled to the power source(s) 106 via an electrical wire(s) 132. In such an embodiment, during operation of the agricultural implement 12, the second electrode(s) 110 is generally in contact with the soil within the field. As such, in some embodiments, a ground-engaging tool(s) other than the shank(s) 46 may correspond to the second electrode(s) 110. For example, in one such embodiment, one or more of the disk blades 50 may correspond to the second electrode(s) 110. Thus, unlike the system 100 of FIG. 4, the system 100 shown in FIG. 5 does not include the electrical wire(s) 120. However, in alternative embodiments, the second electrode(s) 110 may be configured in any suitable manner.

In operation, alternating positive and negative electric fields may be induced on the forward outer surface(s) 76 of the shank(s) 46. More specifically, as the agricultural implement 12 travels across the field, the shank(s) 46 is moved through the soil such that the soil slides over the forward outer surface(s) 76 of the shank(s) 46. During a given period of time, the flow control device(s) 112 is actuated or otherwise adjusted such that the first electrode(s) 108 acts as an anode(s) and the second electrode(s) 110 acts as a cathode(s). In such instances, the power source(s) 106 may cause electric current to flow from the first electrode(s) 108 to the second electrode(s) 110, thereby inducing a positive electric field on the forward outer surface(s) 76 of the shank(s) 46. During a subsequent period of time, the flow control device(s) 112 is again actuated or otherwise adjusted such that the first electrode(s) 108 acts as a cathode(s) and the second electrode(s) 110 acts as an anode(s). In such instances, the power source(s) 106 may cause electric current to flow from the second electrode(s) 110 to the first electrode(s) 108, thereby inducing a negative electric field on the outer surface(s) 76 of the shank(s) 46. During another subsequent period of time, the flow control device(s) 112 is further actuated or otherwise adjusted such that the first electrode(s) 108 acts as an anode(s) and the second electrode(s) 110 acts as a cathode(s) again and so on.

As mentioned above, the alternating positive and negative electric fields induced on the forward outer surface(s) 76 of the shank(s) 46 reduce the wear incurred by the shank(s) 46 during an agricultural operation. More specifically, water generally adheres to the portion(s) of the forward outer surface(s) 76 of the shank(s) 46 that are negatively charged and slides off of portion(s) of the forward outer surface(s) 76 of the shank(s) 46 that are positively charged. Such alternating adherence and a shedding of water on each portion 74, 78 of the forward outer surface(s) 76 of the shank(s) 46 results in electroosmosis, which reduces the adhesional forces between the shank(s) 46 and the soil. This, in turn, reduces the friction between the shank(s) 46 and the soil and, thus, the wear incurred by the shank(s) 46 during an agricultural operation. Reduced wear of the shank(s) 46 increases the service life of the shank(s) 46 and reduces the downtime of the implement 12.

Figure 6:
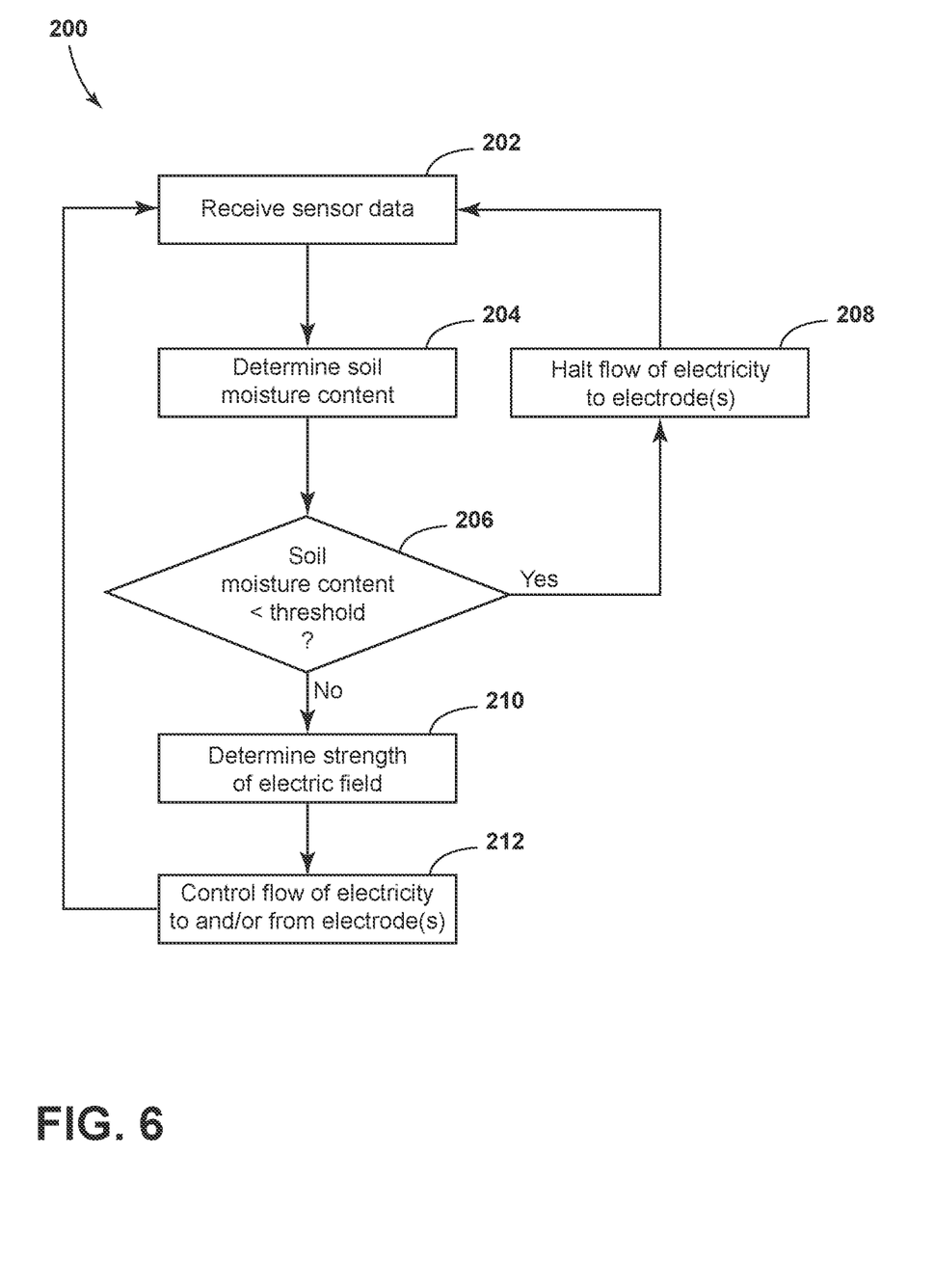
FIG. 6 illustrates a flow diagram providing one embodiment of control logic for reducing shank wear on an agricultural implement in accordance with aspects of the present subject matter.

Referring now to FIG. 6, a flow diagram of one embodiment of example control logic 200 that may be executed by the computing system 122 (or any other suitable computing system) for reducing shank wear on an agricultural implement is illustrated in accordance with aspects of the present subject matter. Specifically, the control logic 200 shown in FIG. 6 is representative of steps of one embodiment of an algorithm that can be executed to reduce shank wear on an agricultural implement without requiring substantial computing resources and/or processing time. However, in other embodiments, the control logic 200 may be used in association with any other suitable system, application, and/or the like for reducing shank wear on an agricultural implement.

As shown, at (202), the control logic 200 includes receiving sensor data indicative of the soil moisture content of a portion of a field. Specifically, as mentioned above, in several embodiments, the computing system 122 may be communicatively coupled to the sensor(s) 102 via the communicative link 128. In this respect, as the vehicle/implement 10/12 travels across the field to perform an agricultural (e.g., tillage) operation thereon, the computing system 122 may receive data from the sensor(s) 102. Such data may, in turn, be indicative of the soil moisture content of one or more portions of the field forward of the agricultural implement 12 (and, more specifically, forward of the shanks 46).

Furthermore, at (204), the control logic 200 includes determining the soil moisture content of the field based on the received sensor data. Specifically, in several embodiments, the computing system 122 may be configured to analyze the sensor data received at (202) to determine the soil moisture content of the portion(s) of the field forward of the agricultural implement 12. For example, in one embodiment, the determined soil moisture content determined at (206) may correspond to a volumetric soil moisture content value for the section(s) of the field positioned within the field(s) of view 106 of the sensor(s) 102, such as at the penetration depth of the shanks(s) 46. In this respect, the computing system 122 may use one or more look-up tables, mathematical formulas, and/or algorithms stored within its memory device(s) 130 to correlate the received sensor data to corresponding soil moisture content values. As will be described below, the determined soil moisture content is used to control the flow of electricity to and/or from the first electrode(s) 108 and/or the second electrode(s) 110 such that an electric field(s) is induced on at least a portion of the forward outer surface(s) 76 of the shanks(s) 46, thereby reducing the friction between the shanks(s) 46 and soil and, thus, the wear incurred by the shanks(s) 46 during use.

Additionally, at (206), the control logic 200 includes comparing the determined soil moisture content to a predetermined threshold value. Specifically, in several embodiments, the computing system 122 may be configured to compare the soil moisture content determined at (204) to a predetermined threshold value. When the determined soil moisture content falls below the predetermined threshold value, the soil moisture content may be sufficiently low such that the use of electric fields may be ineffective or inefficient at reducing the friction between the shanks(s) 46 and the soil. In such instances, the control logic 200 proceeds to (208). Conversely, when the determined soil moisture content is equal to or exceeds the predetermined threshold value, the soil moisture content may be sufficiently high such that the use of electric fields may be an effective and efficient mechanism to reduce the friction between the shanks(s) 46 and the soil. In such instances, the control logic 200 proceeds to (210).

Moreover, at (208), the control logic 200 includes halting the flow of electricity to and/or from the electrode(s) such that the electric field is not induced on the at least the portion of the forward outer surface of the shank. Specifically, as mentioned above, in several embodiments, the computing system 122 may be communicatively coupled to the flow control device(s) 112 via the communicative link 126. In this respect, when it is determined at (206) that the determined soil moisture content falls below the predetermined threshold value, the computing system 122 may transmit control signals to the flow control device(s) 112 via the communicative link 126. Such control signals may, in turn, instruct the flow control device(s) 112 to prevent the flow of electricity between the first and second electrode(s) 108, 110. This, in turn, prevents an electric field(s) from being induced on the forward outer surface(s) 78 of the shank(s) 46. Upon completion of (208), the control logic 200 returns to (202).

Conversely, at (210), the control logic 200 includes determining the strength of the electric field to be induced on the shank based on the determined soil moisture content. In general, the strength of the electric field that is sufficient to facilitate electroosmosis on the forward outer surface(s) 78 of the shank(s) 46 varies with soil moisture content. Specifically, higher soil moisture content values require greater electric field magnitudes to reduce the adhesional forces and, thus, the friction between the shank(s) 46 and the soil. As such, in several embodiments, the computing system 122 may be configured to determine the strength of the electric field(s) to be induced on the forward outer surface(s) 76 of the shank(s) 46 (e.g., the portions 74 and/or the portions 78) based on the soil moisture content determined at (206). For example, the computing system 122 may use one or more look-up tables, mathematical formulas, and/or algorithms stored within its memory device(s) 130 to correlate the soil moisture content values to corresponding electric field strengths.

In addition, at (212), the control logic 200 includes controlling the flow of electricity such that the electric field induced on the at least the portion of the forward outer surface of the shank has the determined strength. Specifically, in several embodiments, the computing system 122 may be configured to control the operation of the flow control device(s) 112 to control the flow of electricity to and/or from the first electrode(s) 108 and/or the second electrode(s) 110 such that the electric field(s) induced on the portion(s) of the forward outer surface(s) 76 of the shank(s) 46 has the strength determined at (210). This, in turn, ensures that the electric field(s) induced on the portion(s) of the forward outer surface(s) 76 of the shank(s) 46 is sufficient to facilitate electroosmosis, thereby reducing the adhesional forces and, thus, the friction between the shank(s) 46 and the soil. For example, the computing system 122 may transmit control signals to the flow control device(s) 112 via the communicative link 126. Such control signals may, in turn, instruct the flow control device(s) 112 to adjust the flow of electricity between the first and second electrode(s) 108, 110 such that the electric field(s) induced on the forward outer surface(s) 76 of the shank(s) 46 is of the determined strength. Upon completion of (212), the control logic 200 returns to (202).

Figure 7:
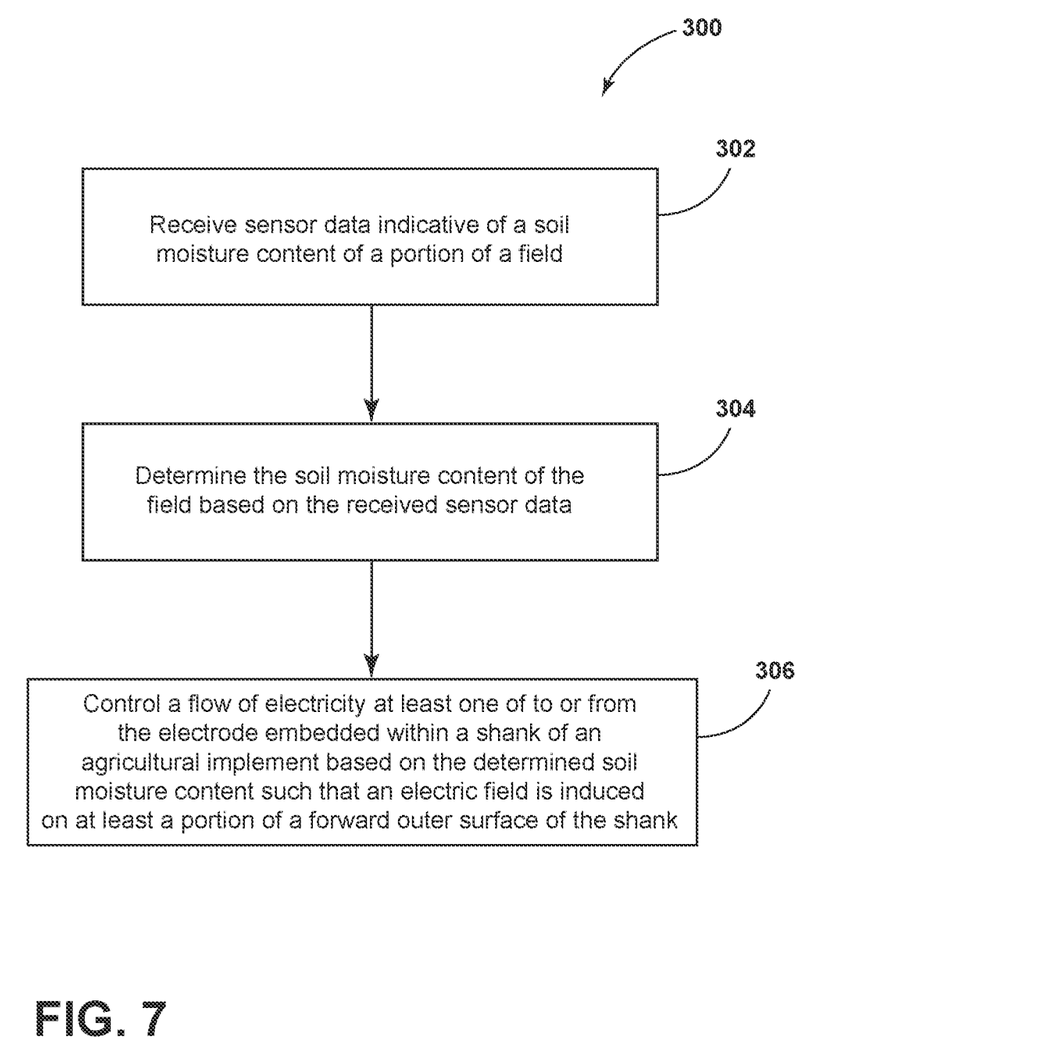
FIG. 7 illustrates a flow diagram of one embodiment of a method for reducing shank wear on an agricultural implement in accordance with aspects of the present subject matter.

Referring now to FIG. 7, a flow diagram of one embodiment of a method 300 for reducing shank wear on an agricultural implement is illustrated in accordance with aspects of the present subject matter. In general, the method 300 will be described herein with reference to the work vehicle 10, the agricultural implement 12, and the system 100 described above with reference to FIGS. 1-6. However, it should be appreciated by those of ordinary skill in the art that the disclosed method 300 may generally be implemented with any work vehicle having any suitable vehicle configuration, with any agricultural implement having any suitable implement configuration, and/or within any system having any suitable system configuration. In addition, although FIG. 7 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 7, at (302), the method 300 includes receiving, with a computing system, sensor data indicative of a soil moisture content of a portion of a field. For instance, as described above, the computing system 122 may be configured to receive data from the sensor(s) 102 as the vehicle/implement 10/12 travels across the field (e.g., to perform an agricultural operation thereon). Such sensor data is, in turn, indicative of the soil moisture content of a portion(s) of the field positioned forward of the agricultural implement 12.

Furthermore, at (304), the method 300 includes determining, with the computing system, the soil moisture content of the field based on the received sensor data. For instance, as described above, the computing system 122 may be configured to determine the soil moisture content of the field based on the received sensor data.

Additionally, at (306), the method 300 includes controlling, with the computing system, the flow of electricity at least one of to or from an electrode embedded within a shank of an agricultural implement based on the determined soil moisture content such that an electric field is induced on at least a portion of a surface of the shank. For instance, as described above, the computing system 122 may be configured to control the operation of the flow control device(s) 112 to control the flow of electricity to and/or from the first electrode(s) 108 and/or the second electrode(s) 112 based on the determined soil moisture content such that an electric field(s) is induced on at least a portion of the forward outer surface(s) 76 of the shank(s) 46 (e.g., of a sufficient strength to facilitate electroosmosis and the associated reduction/prevention of friction between the shank(s) 46 and the soil).

It is to be understood that the steps of the control logic 200 and the method 300 are performed by the computing system 122 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the computing system 122 described herein, such as the control logic 200 and the method 300, is implemented in software code or instructions which are tangibly stored on a tangible computer readable medium. The computing system 122 loads the software code or instructions via a direct interface with the computer readable medium or via a wired and/or wireless network. Upon loading and executing such software code or instructions by the computing system 122, the computing system 122 may perform any of the functionality of the computing system 122 described herein, including any steps of the control logic 200 and the method 300 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

The invention claimed is:

1. An agricultural implement, comprising:
a frame;
a shank supported on the frame, the shank configured to be moved through soil within a field as the agricultural implement travels across the field;
an electrode embedded within the shank;
a sensor configured to generate data indicative of a soil moisture content of a portion of the field; and
a computing system communicatively coupled to the sensor, wherein the computing system:
determines the soil moisture content of the field based on the data generated by the sensor;
determines a strength of an electric field to be induced on at least a portion of a forward outer surface of the shank based on the determined soil moisture content to ensure electroosmosis occurs on the shank;
controls a flow of electricity at least one of to or from the electrode such that the electric field of the determined strength is induced on at least a portion of a forward outer surface of the shank.

2. The agricultural implement of claim 1, wherein, when controlling the flow of electricity, the computing system:
compares the determined soil moisture content to a predetermined threshold value; and
when the determined soil moisture content falls below the predetermined threshold value, halts the flow of electricity at least one of to or from the electrode such that the electric field is not induced on the at least the portion of the forward outer surface of the shank.

3. The agricultural implement of claim 1, wherein the sensor has a field of view directed at a section of the field positioned forward of the agricultural implement relative to a direction of travel of the agricultural implement.

4. The agricultural implement of claim 3, wherein, when determining the soil moisture content of the field, the computing system determines a volumetric soil moisture content value for the section of the field positioned within the field of view of the sensor.

5. A system for reducing shank wear on an agricultural implement, the system comprising:
a shank configured to be moved through soil within a field as the agricultural implement travels across the field;
an electrode embedded within the shank;
a sensor configured to generate data indicative of a soil moisture content of a portion of the field; and
a computing system communicatively coupled to the sensor, wherein the computing system:
determines the soil moisture content of the field based on the data generated by the sensor;
determines a strength of an electric field to be induced on at least a portion of a forward outer surface of the shank based on the determined soil moisture content to ensure electroosmosis occurs on the shank;
controls a flow of electricity at least one of to or from the electrode such that the electric field of the determined strength is induced on at least a portion of a forward outer surface of the shank.

6. The system of claim 5, wherein, when controlling the flow of electricity, the computing system:
compares the determined soil moisture content to a predetermined threshold value; and
when the determined soil moisture content falls below the predetermined threshold value, halts the flow of electricity at least one of to or from the electrode such that the electric field is not induced on the at least the portion of the forward outer surface of the shank.

7. The system of claim 5, wherein the sensor has a field of view directed at a section of the field positioned forward of the agricultural implement relative to a direction of travel of the agricultural implement.

8. The system of claim 7, wherein, when determining the soil moisture content of the field, the computing system determines a volumetric soil moisture content value for the section of the field positioned within the field of view of the sensor.

9. The system of claim 8, wherein, when determining the soil moisture content of the field, the computing system determines the volumetric soil moisture content value for the section of the field positioned within the field of view of the sensor at a penetration depth of the shank.

10. The system of claim 7, wherein the sensor is mounted on the agricultural implement.

11. The system of claim 7, wherein the sensor is mounted on a work vehicle configured to tow the agricultural implement across the field.

12. The system of claim 5, wherein the electrode corresponds to a first electrode, the system further comprising:
a second electrode embedded within the shank, the second electrode being spaced apart from the first electrode along a lateral direction of the shank.

13. The system of claim 12, wherein:
the electric field induced on at least the portion of the surface of the shank corresponds to a first electric field induced on a first portion of the forward outer surface of the shank; and
the computing system controls a flow of electricity at least one of to or from the second electrode based on the determined soil moisture content such that a second electric field is induced on a second portion of the forward outer surface of the shank, the second portion of the shank being spaced apart from the first portion of the shank in the lateral direction.

14. The system of claim 13, wherein the first electric field is one of a positive electric field or a negative electric field and the second electric field is the other of the positive electric field or the negative electric field.

15. The system of claim 5, wherein the electrode corresponds to a first electrode, the system further comprising:
a second electrode positioned remote from the shank.

16. A method for reducing shank wear on an agricultural implement, the agricultural implement including a shank configured to be moved through soil within a field as the agricultural implement travels across the field, the agricultural implement further including an electrode embedded within the shank, the method comprising:
receiving, with a computing system, sensor data indicative of a soil moisture content of a portion of the field;
determining, with the computing system, the soil moisture content of the field based on the received sensor data;
determining, with the computing system, a strength of an electric field to be induced on at least a portion of a forward outer surface of the shank based on the determined soil moisture content to ensure electroosmosis occurs on the shank;
controlling, with the computing system, a flow of electricity at least one of to or from the electrode such that an electric field of the determined strength is induced on at least a portion of a forward outer surface of the shank.

17. The method of claim 16, wherein controlling the flow of electricity comprises:
  comparing, with the computing system, the determined soil moisture content to a predetermined threshold value; and
  when the determined soil moisture content falls below the predetermined threshold value, halting, with the computing system, the flow of electricity at least one of to or from the electrode such that the electric field is not induced on the at least the portion of the forward outer surface of the shank.

* * * * *